United States Patent [19]

Cha et al.

[11] Patent Number: 5,702,717
[45] Date of Patent: Dec. 30, 1997

[54] THERMOSENSITIVE BIODEGRADABLE POLYMERS BASED ON POLY(ETHER-ESTER)BLOCK COPOLYMERS

[75] Inventors: Younsik Cha; Young Kweon Choi, both of Salt Lake City, Utah; You Han Bae, Kwangju, Rep. of Korea

[73] Assignee: Macromed, Inc., Salt Lake City, Utah

[21] Appl. No.: 548,185

[22] Filed: Oct. 25, 1995

[51] Int. Cl.$^6$ .............................. A61K 9/10; A61K 9/16
[52] U.S. Cl. ..................... 424/425; 424/426; 424/424; 424/486; 424/501; 604/891.1
[58] Field of Search ................... 424/424, 425, 424/426, 486, 501; 604/890.1, 891.1, 892.1

[56] References Cited

U.S. PATENT DOCUMENTS

| | | | |
|---|---|---|---|
| 4,438,253 | 3/1984 | Casey et al. | 528/86 |
| 4,526,938 | 7/1985 | Churchill et al. | 525/415 |
| 4,652,441 | 3/1987 | Okada et al. | 424/19 |
| 4,745,160 | 5/1988 | Churchill et al. | 525/415 |
| 4,938,763 | 7/1990 | Dunn et al. | 604/891.1 |
| 5,100,669 | 3/1992 | Hyon et al. | 424/426 |
| 5,278,202 | 1/1994 | Dunn et al. | 523/113 |
| 5,324,519 | 6/1994 | Dunn et al. | 424/426 |
| 5,330,768 | 7/1994 | Park et al. | 424/501 |

FOREIGN PATENT DOCUMENTS

| | | |
|---|---|---|
| 0 092 918 | 3/1983 | European Pat. Off. . |
| 0 258 780 | 8/1987 | European Pat. Off. . |
| 2-78629 | 4/1990 | Japan . |
| GB93/01079 | 5/1992 | WIPO . |

OTHER PUBLICATIONS

"Rapidly Degraded Terpolymers of di–Lactide, Glycolide and ε–Caprolactone with Increased hydrophilicity by Copolymerization with Polyethers" Amarprett S. Sawhney and Jeffrey A. Hubbell; Department of Chemical Engineering, University of Texas.

"Inulin Disposition Following Intramuscular Administration of an Inulin/Poloxamer Gel Matrix" Thomas P. Johnston and Susan C. Miller; Journal of Parenteral Science & Technology vol. 43, No. 6 / Nov.–Dec. 1989.

"Sustained Delivery of Interleukin-2 from a Poloxamer 407 Gel Matrix Following Intraperitoneal Injection in Mice" Thomas P. Johnston, Monika A. Punjabi, and Christopher J. Froelich; Pharmaceutical Research, vol. 9 No. 3, 1992.

"Bioerodible Hydrogels Based on Photopolymerized Poly(ethyleneglycol)–co–poly(α–hydroxyacid) Diacrylate Macromers" Amarpreet S. Sawhney, Chandrashekhar P. Pathak, and Jeffrey A. Hubbell; Macromolecules, vol. 26, No. 4, 1993.

"Angiopeptin as a Potent Inhibitor of Myointimal Hyperplasia" Takehisa Matsuda, Noboru Motomura and Takashi Oka; ASAIO Journal 1993.

"Micellisation and Gelation of Triblock Copolymer of Ethylene Oxide and α–Caprolactone, $CL_nE_mCL_n$, in Aqueous Solution." Luigi Martini, David Attwood, John H. Collette, Christian V. Nicholas, Siriporn Tanodekaew, Nan–Jie Deng, Frank Heatley and Colin Booth; J. Chem. SOC. Faraday Trans. 1994.

"Enhancement of Therapeutic Effects of Recombinant Interleukin 2 on a Transplantable Rat Fibrosarcoma by the Use of a Sustained Release Vehicle, Pluronic Gel." Kiyoshi Morikawa, Futoshi Okada, Masuo Hosokawa, and Hiroshi Kobayashi; Cancer Research 47, 37–41, Jan. 1, 1987.

"Toxicological Evaluation of Poloxamer Vehicles for Intramuscular Use." Thomas P. Johnston and Susan C. Miller; Journal of Parenteral Science and technology vol. 39, No. 2 / Mar.–Apr. 1985.

"In–vitro degradation and bovine serum albumin release of the ABA triblock copolymers consisting of poly (L(+)lactic acid), or poly (L(+)lactic acid–co–glycolic acid) A–blocks attached to central polyoxyethylene B–blocks" Li Youxin, Christian Volland, Thomas Kissel; Journal of Controlled Release 32 (1994).

"Synthesis and properties of biodegradable ABA triblock copolymers consisting of poly (L–lactic acid) or poly(L–lactic–co–glycolic acid) A–blocks attached to central poly (oxyethylene) B–blocks" Li Youxin and Thomas Kissel; Journal of Controlled Release, 27 (1993).

"Sustained–Release of Urease from a Poloxamer Gel Matrix". K.A. Fults and T.P. Johnston; Journal of Parenteral Science & Technology vol. 44, No. 2/Mar.–Apr. 1990.

*Primary Examiner*—Ralph H. Dean
*Attorney, Agent, or Firm*—Thorpe, North & Western, L.L.P.

[57] ABSTRACT

A system and method for the parenteral delivery of a drug in a biodegradable polymeric matrix to a warm blooded animal as a liquid with the resultant formation of a gel depot for the controlled release of the drug. The system comprises an injectable biodegradable block copolymeric drug delivery liquid having reverse thermal gelation properties. The delivery liquid is an aqueous solution having dissolved or dispersed therein an effective amount of a drug intimately contained in a biodegradable block copolymer matrix. The copolymer has a reverse gelation temperature below the body temperature of the animal to which it is administered and is made up of (i) a hydrophobic A polymer block comprising a member selected from the group consisting of poly(α-hydroxy acids) and poly(ethylene carbonates) and (ii) a hydrophilic B polymer block comprising a polyethylene glycol. Prior to use the liquid is maintained at a temperature below the reverse gelation temperature of the block copolymer. The liquid is parenterally administered into the animal by intramuscular, intraperitoneal, subcutaneous or similar injection with the liquid forming a gel depot of the drug and biodegradable block polymer as the temperature of the liquid is raised by the body temperature of the animal the reverse gelation temperature of the block copolymer. The drug is released at a controlled rate from the copolymer which biodegrades into non-toxic products. The degradation rate can be adjusted by proper selection of the poly(α-hydroxy acid) utilized in forming the biodegradable hydrophilic A block.

32 Claims, No Drawings ium and to utilize these
THERMOSENSITIVE BIODEGRADABLE POLYMERS BASED ON POLY(ETHER-ESTER)BLOCK COPOLYMERS The present invention relates to the preparation of thermosensitive biodegradable polymers and their use for parenteral administration of peptide and protein drugs. More particularly, this invention relates to thermosensitive biodegradable polymers containing peptide or protein drugs and to a process for preparing the same. This invention is made possible by the use of thermosensitive biodegradable polymers based on poly(ether-ester) block copolymers, which are described in detail hereinafter. The system is based the discovery that poly(ether-ester) block copolymers having certain molecular weight and composition ranges exist as a clear solution at, or about, ambient temperature in water but, when the temperature is raised to about body temperature, interact to form a semi-solid gel, emulsion or suspension.

BACKGROUND OF THE INVENTION AND SUMMARY OF PRIOR ART

Recently, many peptide/protein drugs, effective for a variety of therapeutic applications, have become commercially available through advances in recombinant DNA and other technologies. However, as polypeptides or proteins, their high molecular weight, degradation in the gastrointestinal tract, and short half-life in the body limits their routes of administration to intravenous or intramuscular and subcutaneous injection. And in many cases, daily injection is required for an extended period of time to get the expected therapeutic effect. Long term controlled delivery of such polypeptides or proteins is essential to provide for practical applications of these medications and to utilize these advances in biotechnology. Another problem is patient compliance. It is often difficult to get a patient to follow a prescribed dosage regimen, particularly when the prescription is for a chronic disorder and the drug has acute side-effects. Therefore, it would be highly desirable to provide a system for the delivery of drugs, and polypeptide and protein drugs in particular, at controlled rate over a specified period of time, without the above mentioned problems, in order to increase the therapeutic efficacy, the bioavailability and the patient compliance.

Drug-loaded polymeric devices are being investigated for long term, therapeutic treatment of different diseases. An important property of the polymeric device is biodegradability; meaning that the polymer can break down or degrade within the body to non-toxic components after all drug has been released. Furthermore, techniques, procedures, and solvents used to fabricate the device and load the drug should be safe for the patient, prevent irritation to surrounding tissue, and be a harmless medium for the peptide and protein drugs. Currently, biodegradable implantable controlled release devices are fabricated from crystalline polymers of polyglycolic or polylactic acids. Due to the hydrophobic properties of these polymers, drug loading and device fabrication using this material requires organic solvents such as methylene chloride, chloroform, acetic acid or dimethyl formamide. Obviously extensive drying is required after this process. In most cases, the final polymeric device is fabricated in a distinct solid shape (sphere, slab or rod) requiring surgical implantation, and resulting in tissue irritation.

Currently, there are not many synthetic or natural polymeric materials which can be used for the controlled delivery of peptide and protein drugs because of the strict regulatory compliance requirements, such as biocompatibility, clear degradation pathway and safety of degradation products. The most widely investigated and advanced biodegradable polymers in regard to available toxicological and clinical data are the aliphatic poly($\alpha$-hydroxy acids), such as poly(d,l- or l-lactic acid) (PLA) and poly(glycolic acid) (PGA) and their copolymers. These polymers are commercially available and are presently being used as bioerodable sutures in surgery. The first FDA-approved system for controlled release of peptides, the Lupron Depot™, is also based on lactic acid-glycolic acid copolymers. The Lupron Depot™ consists of injectable microcapsules, which release leuprolide acetate over a prolonged period (e.g., about 30 days) for the treatment of prostate cancer. Based on this history of use, lactic acid-glycolic acid copolymers have been the materials of choice in the initial design of parenteral sustained release delivery systems using a biodegradable carrier.

However, even though there has been some limited success, these polymers also have problems associated with their physicochemical properties and methods of fabrication. Hydrophilic macromolecules, such as polypeptides, cannot diffuse out through the hydrophobic matrix or membrane of polylactides. Drug loading and device fabrication using polylactide requires organic solvents and the solid dosage form may induce tissue irritation.

A. S. Sawhney and J. A. Hubbell, *J. Biomed. Mat. Res.*, 24, 1197–1411 (1990), synthesized terpolymers of d,l-lactide, glycolide and $\epsilon$-caprolactone which degrade rapidly in vitro. For example, a terpolymer composition of 60% glycolide, 30% lactide, and 10% $\epsilon$-caprolactone exhibited a half-life of 17 days. The hydrophilicity of the material was increased by copolymerization with a polyether surfactant prepolymer (Pluronic F-68). This prepolymer is a block copolymer comprising about 80% w. of a hydrophobic poly(propylene oxide) block and 20% w. of a hydrophilic poly(ethylene oxide) block. Copolymerization with the surfactant prepolymer resulted in a stronger and partly crystalline material which was mechanically stable at physiological temperature (e.g. $\approx$37° C.) in water. The half-life of this copolymer was slightly increased compared to the base polymer. However, it is known that Pluronic type of polymeric surfactants, particularly the poly(propylene oxide) block portions, are not biodegradable.

Other implantable delivery systems, such as shown in Dunn et al, U.S. Pat. Nos. 4,938,763 and 5,278,202, have also been known for some time. One unique aspect of such formulations is the fact that, when formulated, they maintain a liquid consistency which allows injection using 22/23 gauge needle. These polymers are either thermoplastic or thermosetting. The thermoplastic system involves the forming of a polymeric solution in a suitable solvent. When the polymeric solution is injected into the body and is exposed to body fluids or water, the solvent diffuses away from the polymer-drug mixture and water diffuses into the mixture where it coagulates the polymer encapsulating the drug within the polymeric matrix as the implant solidifies. The thermoplastic solution requires the use of an organic solvent such as N-methyl-2-pyrrolidone, methyl ethyl ketone, dimethylformamide, propylene glycol, THF, DMSO, dodecylazacycloheptan-2-one (Azone) and the like. The thermosetting system comprises the synthesis of crosslinkable polymers which can be formed and cured in-situ through the use of a curing agent. The polymers are first formed using a polyol initiator and catalyst to form polyol-terminated prepolymers which are further converted to acrylic ester-terminated prepolymers. Just prior to injection, the acrylic prepolymer solution has added thereto a curing agent such as benzoyl peroxide or azobisisobutyronitrile. Once injected, the crosslinking reaction proceeds until sufficient molecular weight has been obtained to cause the polymer to solidify. These polymers are formed primarily by the polymerization or copolymerization of biodegradable hydrophobic polylactides, polyglycolides, polycaprolactones and the like. The polymer type used has degradation times in the range of weeks to months. The degradation rate can be adjusted by choosing the appropriate polymer. The polymers are non-toxic and are well tolerated by the body and the system is easy to formulate. These polymer formulations provide a novel approach for a biodegradable implant since they can be easily injected, avoiding the use of surgical procedures. Their biocompatibility and biodegradability is also well established. The gel matrix once formed will release the drug in a controlled manner and then degrade to products which are easily metabolized and excreted. These thermosetting and thermoplastic formulations incorporate the advantages of an implant while circumventing the need for surgery prior to administration or after the release is complete. However, the major drawback of the thermoplastic formulations is the use of organic solvents which can be toxic or irritating to the body tissues. The thermosetting system requires that the drug be admixed with the prepolymer solution prior to additions of the catalysts because the curing reaction is quite rapid and injection must take place almost immediately following the addition of the curing agent.

An optimum material for use as an injectable or implantable polymeric drug delivery device should be biodegradable, be compatible with hydrophilic or hydrophobic drugs, and allow fabrication with simple, safe solvents, such as water and not require additional polymerization or reaction following administration.

One system, which can be fabricated in aqueous solution, is a class of block copolymers composed of two different polymer blocks, i.e. hydrophilic poly(ethylene oxide) blocks and hydrophobic poly(propylene oxide) blocks. These are synthesized to make up a triblock of poly(ethylene oxide)-poly(propylene oxide)-poly(ethylene oxide) and marketed under the Pluronic™ or Poloxamer™ tradenames. The triblock copolymers absorb water to form gels which have potential for use in topical pharmaceutical and cosmetic systems, i.e. in topical drug delivery systems. These are surface-active block copolymers which exhibit reverse thermal gelation behavior and possess drug release characteristics. However, the Pluronic system is non-biodegradable and its gel properties and drug release kinetics are in need of substantial improvement.

The Pluronic™, Poloxamer™ type triblock copolymers undergo solidification or gelation as the temperature of the solution is raised above a critical temperature (gelation temperature). These polymers form micelles (microscopic spheres incorporating water) at low concentration and turn into thick, continuous gels at high concentrations and elevated temperature (≈30° C.).

As shown in Table 1, the Pluronic-6™ series, including Pluronic F-68™, form a gel at a minimum concentration of 50–60% (w/w) at room temperature, Pluronic F-88™ forms a gel at 40% at 25° C., and Pluronic F-108™ forms a gel at 30% concentration. The thermal gelation mechanism can be explained by micellar desolvation and swelling to form a pseudo-cross-linking among the polymer micelles. The mechanism of gelation involves the incorporation of polymer molecules into micelles as a function of temperature. As the micelle size increases with temperature, the micelles may undergo a thermally induced swelling (micellar enlargement) together with a desolvation of the inner polymer core. This swelling has been associated with conformational changes in the methyl groups of the polyoxypropylene chain. This phenomena is enhanced by hydrophobic polymer interactions at higher temperatures, resulting in a physically entangled, stable network. The network between the polymer molecules produces a progressive increase of the viscosity and the consistency of the vehicle upon heating.

TABLE 1

Physicochemical characteristics and gel-forming property of selected Pluronics ™

|  | F-68 | F-88 | F-98 | F-108 | F-127 |
|---|---|---|---|---|---|
| Molecular weight | 8350 | 10800 | 13500 | 15500 | 11500 |
| PEO:PPO wt. ratio | 80:20 | 80:20 | 80:20 | 80:20 | 70:30 |
| PPO weight | 1750 | 2250 | 2750 | 3250 | 3850 |
| Melting point (°C.) | 50 | 55 | 56 | 57 | 56 |
| Conc (%) and Temp (°C.) |  |  |  |  |  |
| 20% at 25°C. | − | − | − | − | + |
| 20% at 37°C. | − | − | + | + | + |
| 30% at 25°C. | − | − | + | + | + |
| 30% at 37°C. | − | + | + | + | + |
| 40% at 25°C. | − | + | + | + | + |
| 40% at 37°C. | + | + | + | + | + |

PEO: poly(ethylene oxide)
PPO: poly(propylene oxide)
−: no gel-formation
+: gel-formation Pluronic F-127™ (Poloxamer 407™) is one of the least toxic of the block copolymers and forms a gel at only 20% concentration in water, at 20° C. Pluronic F-127™ consists by weight of approximately 70% ethylene oxide and 30% propylene oxide with an average molecular weight of 11500. The unique characteristics of this polymer is reverse thermal gelation; concentrated solutions (20–30 wt/wt %) of the copolymer are fluid at low temperature (under 10° C.), but are soft gel at body temperature.

Potentially, protein drugs could be loaded into these types of gels simply by increasing the temperature of an aqueous solution of protein and polymer, thereby trapping and incorporating the protein with the gel network. Since the solvent is water, the bioactivity of the protein should be preserved and the release rate of the protein from the gel could be controlled.

Several studies have been done on the usefulness of Pluronic F-127™ gels as an injectable, sustained release depot. Toxicological evaluation of Pluronic™ vehicles following intramuscular (i.m.) injections in rabbits has been reported, T. P. Johnson et al., J. Parenteral Sci. & Tech., Vol. 39, No. 2, pp 83–88 (1985). Sustained release of urease from a Poloxamer™ gel matrix has also been reported, T. P. Johnson et al., J. Parenteral Sci. a Tech., Vol. 44, No. 2, pp 58–65 (1990). The sustained delivery of IL-2 from a Poloxamer 407™ gel matrix following intraperitoneal (i.p.) injection in mice is reported in T. P. Johnson et al., Pharmaceutical Research, Vol. 9, No. 3, pp. 425–434 (1992). Subcutaneous (s.c.) injection of IL-2 in 30% (w/w) Pluronic F-127™ enhanced antitumor immune responses by sustained IL-2 activity at the tumor sites as reported by K. Morikawa et al. Cancer Research, 47, 37–41 (1987). An alteration of the rat kidney to efficiently clear inulin by means of glomerular filtration was observed after i.m. injection of inulin-Pluronic™ gel formulations was described by K. F. Fults et al., J. Parental Sci. & Tech., Vol. 43, No. 6, 279–285 (1989).

There is a strong need for hydrophilic biodegradable materials which can be used to incorporate water-soluble polypeptide drugs in solution. A. S. Sawhney et al., Macromolecules, Vol 26, No. 4, 581–589 (1993) synthesized macromers having a poly(ethylene glycol) central block, extended with oligomers of α-hydroxy acids such as oligo (d,l-lactic acid) or oligo(glycolic acid) and terminated with acrylate groups. Using non-toxic photoinitiators, the macromers can be rapidly polymerized with visible light. Due to the multifunctionality of the macromers, polymerization results in the formation of crosslinked gels. The gels degrade upon hydrolysis of the oligo(α-hydroxy acid) regions into poly(ethylene glycol), the α-hydroxy acid, and oligo(acrylic acid) and their degradation rates can be tailored by appropriate choice of the oligo(α-hydroxy acid) from less than 1 day to up to 4 months. However, in this system, a photoinitiator, an additional component, is employed as well as an additional process such as photocrosslinking.

Okada et al., Japanese Patent 2-78629 (1990), synthesized biodegradable block copolymeric materials by transesterification of poly(lactic acid) (PLA) or poly(lactic acid)/ glycolic acid (PLA/GA) and poly(ethylene glycol) (PEG). The molecular weight range for PLA/GA was 400 to 5,000 and for PEG, 200 to 2,000. The mixture was heated at 100° to 250° C. for 1 to 20 hours under a nitrogen atmosphere. The product was miscible with water and formed a hydrogel. It also precipitated in water above room temperature depending on the composition. In other words, it is possible to change the water-solubility and hydrophobicity by exposing the polymer solution to elevated temperatures. The molecular structure of the product obtained cannot be defined based on the description given. However, the typical experimental conditions were: 30 g of poly(d,l-lactic acid) (MW 1590) was mixed with 20 g PEG (MW 570–630) and heated in a molten state without the use of any solvent at 250° C. under nitrogen for 4.5 hours. The resulting product was immediately dissolved by dispersing it in 300 ml ice-water. A white polymer precipitate was obtained by heating the dispersion to 50° C. The polymer was purified by repeating this process and dried at 50° C. under vacuum to obtain a semi-waxy material. The materials can be mixed with various peptide and protein solutions and used as an injectable sustained release formulation. It can also be freeze-dried to make a solid block, or vacuum dried to make a paste, which can be implanted. It can also be used as a mixture with other biocompatible materials or microporous materials such as hydroxyapatite.

T. Matsuda, ASAIO Journal, M512–M517 (1993) used a biodegradable polymeric gel to deliver a potent peptidyl antiproliferative agent, angiopeptin, to prevent the myointimal hyperplasia that occurs when a diseased vessel is replaced with an artificial graft or treated by an intravascular device. A highly viscous liquid of a block copolymer composed of poly(lactic acid) and poly(ethylene glycol) (PLA-PEG) block segments was used as an in situ coatable drug carrier. The materials were supplied by Taki Chemical Co., Ltd., Hyogo, Japan. A prolonged slow release of angiopeptin from the polymer gel, consisting of 0.5 g PLA-PEG and 0.5 mg angiopeptin, was observed in vitro over a few weeks when the gel was kept in a buffer solution maintained at 37° C. No early burst release of angiopeptin was observed. Based on these results, the local sustained angiopeptin release from the biodegradable polymeric gel coated on an injured vessel in vivo was theorized to be effective.

L. Martini et al., J. Chem. Soc., Faraday Trans., 90(13), 1961–1966 (1994) synthesized very low molecular weight ABA type triblock copolymers by incorporating hydrophobic poly(ε-caprolactone) which is known to be subject to degradation in vivo by hydrolytic chain scission involving the ester linkages and reported the solution properties of the PCL-PEG-PCL block copolymers. Clouding was observed visually when an aqueous solution of the block copolymers were slowly heated. The cloud points of 2 wt % aqueous solutions of the copolymers were 65° C. and 55° C. for PCL-PEG-PCL (450:4000:450) and PCL-PEG-PCL (680:4000:680) respectively. Reversible gelation on cooling solutions of PCL-PEG-PCL (680:4000:680) was observed at critical concentrations and temperatures ranging from 13% at 25° C. to 30% at 80° C. No lower gel-sol transition was observed on further cooling the solutions to 0° C. The gelation of a micellar solution of a triblock copolymer of caprolactone and oxyethylene, as with that of micellar solutions Of oxyethylene/oxypropylene and oxyethylene/ oxybutylene copolymers, is almost an athermal process. The in vitro degradation rate of PCL-PEG-PCL (680:4000:680) was very slow. Only ca. 20% decrease in molar mass (from GPC) was observed over a period of 16 weeks.

OBJECTS AND SUMMARY OF THE INVENTION

It is an object of the present invention to provide block copolymer drug delivery systems that are biodegradable, exhibit reverse thermal gelation behavior and possess good drug release characteristics.

It is also an object of this invention to provide methods to fabricate copolymeric biodegradable thermosensitive peptide or other drug delivery devices.

A still further object of this invention is to provide a drug delivery system for the parenteral administration of hydrophilic drugs and particularly highly water-soluble peptide and protein drugs.

Yet another object of this invention is to provide a method for the parenteral administration of drugs in a biodegradable polymeric matrix resulting in the formation of a gel depot within the body from which the drugs are released at a controlled rate with the corresponding biodegradation of the polymeric matrix.

These and other objects will become apparent from the following summary and detailed description of the various embodiments making up this invention.

As used herein the following terms shall have the assigned meanings:

"Parenteral" shall mean any route of administration other than the alimentary canal and shall specifically include intramuscular, intraperitoneal, intra-abdominal, subcutaneous, and, to the extent feasible, intravenous.

"Solution", "aqueous solution" and the like, when used in reference to a combination of drug and biodegradable block copolymer contained in such solution, shall mean a water based solution having such drug/polymer combination dissolved or uniformly suspended therein at a functional concentration and maintained at a temperature below the LCST of the block copolymer.

"Drug delivery liquid" or "drug delivery liquid having reverse thermal gelation properties" shall means a "solution" suitable for injection into a warm-blooded animal which forms a depot upon having the temperature raised above the LCST of the copolymer.

"Depot" means a drug delivery liquid following injection into a warm-blooded animal which has formed a gel upon the temperature being raised to or above the LCST.

"LCST, or lower critical solution temperature", means the temperature at which the biodegradable block copolymer undergoes reverse thermal gelation, i.e. the temperature below which the copolymer is soluble in water and above which the block copolymer undergoes phase separation to form a semi-solid containing the drug and the block copolymer.

The terms "LCST", "gelation temperature" and "reverse thermal gelation temperature" or the like shall be used interchangeably in referring to the LCST.

"Gel", when used in reference to a semi-solid combination of drug and biodegradable block copolymer at a temperature at or above the LCST, shall be inclusive of such combinations in the form of gels, emulsions, dispersions, suspensions and the like.

"Biodegradable" meaning that the block polymer can break down or degrade within the body to non-toxic components after all drug has been released.

"Drug" shall mean any organic compound or substance having bioactivity and adapted or used for a therapeutic purpose.

"Peptide", "polypeptide", "oligopeptide" and "protein" shall be used interchangeably when referring to peptide or protein drugs and shall not be limited as to any particular molecular weight, peptide sequence or length, field of bioactivity or therapeutic use unless specifically stated.

"Poly($\alpha$-hydroxy acid)" shall mean a poly($\alpha$-hydroxy acid) polymer per se or a poly($\alpha$-hydroxy acid) polymer or copolymer derived from the ring opening polymerization of an $\alpha$-hydroxy acid precursor, such as a corresponding lactide, glycolide or lactone.

Basic to the present invention is the utilization of a block copolymer having hydrophobic or "A" block segments and hydrophilic or "B" block segments. Generally the block copolymer will be a triblock copolymer, i.e. an ABA or BAB type block copolymer. However, the block copolymer could also be a multiblock copolymer having repeating BA or AB units to make $A(BA)_n$ or $B(AB)_n$ copolymers where n is an integer or from 2 to 5.

The biodegradable hydrophobic, or A block, segment is preferably a poly($\alpha$-hydroxy acid) member derived or selected from the group consisting of poly(d,l-lactide), poly (l-lactide), poly(d,l-lactide-co-glycolide), poly(l-lactide-co-glycolide), poly($\epsilon$-caprolactone), poly($\gamma$-butyrolactone), poly($\delta$-valerolactone), poly($\epsilon$-caprolactone co-lactic acid), poly($\epsilon$-caprolactone-co-glycolic acid-co-lactic acid), hydroxybutyric acid, malic acid and bi- or terpolymers thereof. The above listing is not intended to be all inclusive or necessarily self limiting as combinations or mixtures of the various $\alpha$-hydroxy acids can be used to form homopolymeric or copolymeric hydrophobic block segments and still be within the scope of the invention. The average molecular weight of such $\alpha$-hydroxy acid polymeric blocks is between about 500 and 10,000 and is more preferably between about 500 and 3,000.

Another biodegradable hydrophobic or A block segment can be a low molecular weight enzymatically degradable poly(ethylene carbonate). The average molecular weight of such poly(ethylene carbonate) polymeric blocks is between about 200 and 10,000 and is more preferably between about 200 and 3,000.

The hydrophilic B block segment is preferably polyethylene glycol (PEG) having an average molecular weight of between about 1000 to 20,000 and is more preferably between about 1,000 and 5,000.

Both ABA and BAB type hydrophilic/hydrophobic block copolymers synthesized as disclosed herein possess reverse thermal gelation properties and are biodegradable. BAB type block copolymers possess similarities to the Pluronic system described above, but are quite different in that the hydrophobic poly($\alpha$-hydroxy acid) or poly(ethylene carbonate) A block is biodegradable and more biocompatible than the hydrophobic PPO block of the Pluronic system.

As noted, the B block is formed from various, but appropriate, molecular weights of hydrophilic poly(ethylene glycol) (PEG). PEG was chosen as the hydrophilic water-soluble block domain because of its unique biocompatibility, nontoxicity, micelle forming properties, and rapid clearance from the body.

The hydrophobic A blocks are synthesized and utilized because of their biodegradable and biocompatible properties. The in vitro and in vivo degradation of these hydrophobic polymer blocks is well understood and the degradation products are natural metabolites that are readily eliminated by the body.

The molecular weight of the hydrophobic poly($\alpha$-hydroxy acid) or poly(ethylene carbonate) A blocks, relative to that of the water-soluble B PEG block, is regulated to be sufficiently small to retain desirable water-solubility and gelling properties. Also, the proportionate weight ratios of hydrophilic B block to the hydrophobic A block must also be sufficient to enable the block copolymer to possess water solubility at temperatures below the LCST (lower critical solution temperature). Generally, the PEG block should be at least 50% w. of the block copolymer to remain water-soluble and is perferably higher. Thus, biodegradable block copolymers possessing thermally reversible gelation properties are prepared wherein the hydrophilic B block makes up about 50 to 85% by weight of the copolymer and the hydrophobic A blocks makes up about 15 to 50% by weight of the copolymer.

The concentration at which the block copolymers are soluble at temperatures below the LCST may be considered as the functional concentration. Generally speaking, block copolymer concentrations of up to about 50% by weight can be used and still be functional. However, concentrations in the range of about 3 to 40% are preferred and concentrations in the range of about 10–25% be weight are most preferred. In order to obtain a viable phase transition of the polymer, a certain minimum concentration is required. At the lower functional concentration ranges the phase transition may result in the formation of an emulsion rather than a gel. At higher concentrations, a gel network is formed. The actual concentration at which an emulsion may phase into a gel network may vary according to the ratio of hydrophobic A block to hydrophilic B block and the composition and molecular weights of each of the blocks. Since both emulsions and gels can both be functional it is not imperative that the acutal physical state be precisely determined. However, the formation of a swollen gel network is preferred.

The mixture of the biodegradable polymer and peptide/ protein drugs may be prepared as an aqueous solution at a lower temperature than the gelation temperature of the polymeric material. Once injected into the body via intramuscular, subcutaneous or intraperitoneal route as a liquid, the drug/polymer formulation will undergo a phase change and will preferably form a highly swollen gel, since body temperature will be above the gelation temperature of the material.

This system will cause minimal toxicity and mechanical irritation to the surrounding tissue due to the biocompatibility of the materials and will be completely biodegradable within a specific predetermined time interval. Once gelled, the drug release from the polymeric matrix can be controlled by proper formulation of the various copolymer blocks.

In both of the ABA and BAB copolymer embodiments, a solution of the drug and polymer is prepared and then implanted into the body as a solution which gels or solidifies into a depot as the temperature is raised due to the reverse gelation properties of the drug/polymer composition. It may also be desirable to formulate these compositions for oral use in the form of tablets or capsules.

This may be accomplished by the preparation of microspheres containing peptide or protein drugs by using either the ABA type or BAB type thermosensitive biodegradable block copolymers described above. The thermosensitive polymer solution in cold water is mixed with aqueous solution of peptide/protein drugs and is then added dropwise into a warm oil. The raising of the temperature causes the gelation of the polymer and the drug is entrapped into the solidifying or partially precipitating gel droplets suspended in the warm oil. The solidified droplets become partially hardened microspheres which can then be separated, washed, and dried under vacuum. The resultant microspheres can be loaded into capsules or compressed into tablets to make a sustained release oral dosage form for peptide/protein drugs. The drug loaded microspheres will disintegrate slowly especially at body temperature which is above the gelling point of the polymer.

The only limitation as to how much drug can be loaded onto the copolymer is one of functionality. Generally speaking, the drug can make up between about 0.1 to 10% by weight of the drug polymer combination with ranges of between about 1 to 5% being preferred.

This invention is applicable to polypeptides quite generally, but is most useful for polypeptides which are relatively stable at temperatures of up to about 50° C.

Many labile peptide and protein drugs can be subjected to the reverse thermal gelation encapsulation process described herein.

While not being specifically limited to the following, pharmaceutically useful polypeptides may be selected from group consisting of oxytocin, vasopressin, adrenocorticotrophic hormone, epidermal growth factor, platelet-derived growth factor (PDGF), prolactin, luliberin or luteinising hormone releasing hormone, growth hormone, growth hormone releasing factor, insulin, somatostatin, glucagon, interleukin-2 (IL-2), interferon-$\alpha,\beta,\gamma$ (IFN-$\alpha,\beta,\gamma$), gastrin, tetragastrin, pentagastrin, urogastroine, secretin, calcitonin, enkephalins, endorphins, angiotensins, thyrotropin releasing hormone (TRH), tumor necrosis factor (TNF), nerve growth factor (NGF), granulocyte-colony stimulating factor (G-CSF), granulocyte macrophage-colony stimulating factor (GM-CSF), macrophage-colony stimulating factor (M-CSF), renin, bradykinin, bacitracins, polymixins, colistins, tyrocidin, gramicidines, and synthetic analogues, modifications and pharmacologically active fragments thereof, monoclonal antibodies and soluble vaccines.

The only limitation to the peptide or protein drug which may be utilized is one of functionality.

In some instances, the functionality or physical stability of proteins can also be increased by various additives to aqueous solutions of the peptide or protein drugs. Additives, such as polyols (including sugars), amino acids, proteins such as collagen and gelatin and certain salts may be used. These additives can readily be incorporated into the reverse thermal gelation process of the present invention.

Developments in protein engineering may provide the possibility of increasing the inherent stability of peptide or proteins also. While such resultant engineered or modified proteins may be regarded as new entities in regards to regulatory implications, that does not alter their suitability for use in the present invention. One of the typical examples of modification is PEGylation of polypeptides. The stability of the polypeptide drugs can be significantly improved by covalently conjugating water-soluble polymers such as polyethylene glycol with the polypeptide. Another example is the modification of the aminoacid sequence in terms of the identity or location of one or more residues by terminal and internal addition and deletion or substitution (e.g., deletion of cysteine residues or replacement by alanine or serine).

Any improvement in stability enables a therapeutically effective polypeptide or protein to be continuously released over a prolonged period of time following a single administration of the pharmaceutical composition to a patient.

In addition to peptide or protein based drugs, other drugs, at similar concentratons, may be utilized such as anticancer agents, antibiotics, antiinflammatory agents, hormones, and the like. Typical anticancer agents include adriamycin, mitomycin, bleomycin, cisplatin, carboplatin, doxorubicin, daunorubicin, 5-fluorouracil, methotrexate, taxol, taxotere, actinomycin D and the like.

If desired, the degradation rate of the block copolymer may be modified as desired to release the drug over a predetermined time period. This may be accomplished by the introduction of a bi- or terpolymer structure into the hydrophobic segment.

Different poly($\alpha$-hydroxy acids) degrade at different rates. For example, the hydrophobic poly($\epsilon$-caprolactone) segment in the block copolymer degrades very slowly. The primary hydrolyric degradation product of poly($\epsilon$-caprolactone) is 6-hydroxyhexanoic acid. Studies with tritium labeled poly ($\epsilon$-caprolactone) showed that about 70% of the excreted radioactivity is in the form of tritiated water which indicates a substantial metabolism of 6-hydroxyhexanoic acid. The metabolic pathway for 6-hydroxyhexanoic acid can be deduced from the metabolic pathways established for hexanoic acid and adipic acid. 6-Hydroxyhexanoic acid is mainly transformed to adipic acid by $\omega$-oxidation in the microsomes of liver and kidney. The adipic acid is then metabolized by $\beta$-oxidation in much the same fashion as fatty acids yielding predominantly carbon dioxide and water.

Based on the above, one would expect that the hydrophobic poly($\epsilon$-caprolactone) segment in a PCL-PEG-PCL block copolymer to degrade very slowly. For optimal use in a polymeric drug delivery system, it is desirable to see no polymeric materials are left over after the complete depletion of the drug from the polymer. The degradation rate of the PCL-PEG-PCL block copolymer system can be further modified by incorporating a bi- or terpolymer structure into the hydrophobic PCL segment. For example, incorporation of glycolide and/or lactide units to the PCL segment to form a bi- or terpolymeric poly($\alpha$-hydroxy acid) segment will significantly accelerate the degradation rate of this hydrophobic block copolymer segment.

Other bi- or terpolymeric hydrophobic combinations using different poly($\alpha$-hydroxy acids) can be utilized to derive block segments having desired degradation rates.

Another adaptation in the preparation of thermosensitive drug delivery systems is to utilize the interaction between peptide/protein drugs in contact with these temperature sensitive biodegradable gels. Usually the duration of sustained release from a thermosensitive gel device is not very long. For example, about 8 hours of sustained release was observed after subcutaneous injection of the non-degradable Pluronic F-127™ (PEO-PPO-PEO) gel preparations. The interaction between the peptide/protein drugs and the temperature sensitive biodegradable gels will affect physical/chemical compatibility and bioactivity of the drugs. For example, in the PCL-PEG-PCL or PLA-PEG-PLA type systems, the hydrophobic interaction between the drug and polymer can extend the duration of drug release. Also, the nature of the drug/polymer complexes will change the release kinetics and release duration of the controlled release system. For example, it is known that salt formation between a carboxy terminated polyester and a peptide/protein drug can change the physico-chemical properties of the complex such as its solubility in organic solvents.

It is also possible to modify polymeric system by the incorporation of ionic groups to cause ionic interactions between the drug and polymer to adjust the drug release profile. For example, carboxyl functional groups can be incorporated into the hydrophobic segment of the thermosensitive polymer system by employing malic acid or its derivatives as a comonomer during the synthesis. Other polycarboxylic acids could also be utilized. Thus the acidic group can interact with basic group of peptide/protein drugs. It is also known that the covalent attachment of the hydrophilic polyethylene glycol segment to the protein will increase the stability of the drug in solution and prevent aggregation. It is also known that certain surfactants significantly increase protein stability. The modified hydrophilic-hydrophobic block copolymer which contains ionic groups such as carboxy group therefore serve, not only as a release rate modifier, but also as a stabilizing agent for the labile protein because of the specific drug-polymer interaction.

Another embodiment or approach to the obtaining of thermosensitive polymers having a desired rated of degradation is to incorporate an enzymatically degradable hydrophobic segment in the block copolymer system described in the present invention. This approach has a significant meaning because of the fact that the poly(ether-ester) block copolymer system is hydrolyrically labile and difficult to store for lengthy periods of time in an aqueous environment. It would be desirable to provide a hydrophobic polymeric material which is stable in an aqueous environment in vitro but readily degrades by enzymatic action in vivo. Poly (ethylene carbonate) is one of the best candidate polymers for this purpose. This polymer is flexible at room temperature due to its low glass transition temperature (Tg, 6° C.) and is very hydrophobic. No degradation occurs in water at room temperature i.e. about 37° C. However, a slow decrease of molecular weight is observed when the polymer is treated with a boiling dilute HCl solution. On the other hand, rapid degradation occurred when the polymer is implanted in the animal body. A thick slab (about 300 μm thickness) of a poly(ethylene carbonate) polymer completely disappeared within 2-3 weeks after implantation as noted by T. Kawaguchi et al., *Chem. Pharm. Bull.* 31 (4) 1400 (1983). Surprisingly, no enzymatic degradation occurs at all in the case of poly(propylene carbonate) despite the structural similarity. The rate of enzymatic degradation can be controlled by blending or copolymerization of the poly (ethylene carbonate) and poly(propylene carbonate). When the poly(ethylene carbonate) is hydrolyzed, both ends are terminated with hydroxy group. Various chemical reactions such as isocyanate, acid chloride, N-hydroxy succinimide reactions can be utilized to synthesize ABA or BAB type block or multiblock copolymers described in the present invention.

The synthesized polymers will be characterized for molecular weight, block length, polymer composition, critical micelle concentration, surface activity, gelation temperature, water content of gels, tissue compatibility, and biodegradability of the polymers.

The reverse thermal self-gelling systems described herein are very useful as a vehicle with which to increase the viscosity of a protein formulation and thus, sustain the rate of release of a protein into the systemic circulation following extravascular administration. These polymers will be especially useful for incorporating peptide and protein drugs into polymeric carriers because proteins are sensitive to heat, organic solvents, and changes in pH and ionic strength, and are thus prone to loss in their biological activity. Therefore, a sustained release dosage form can be prepared with these polymers, in which a drug is dissolved (or dispersed) in a cold polymer solution, forming a drug-entrapped semi-solid gel immediately after injection into the body. The polymer/drug mixture can be injected at any site of the body via intramuscular, subcutaneous, or intraperitoneal route. The drug/protein release rates and duration will be a function of solidified gel density, molecular weight of the drug/protein, and other factors such as hydrophobic or ionic interactions. Bulk degradation will occur because the injected gel is hydrophilic and water is present in the bulk of the gel. The polymer will be degraded into small fragments that may or may not be water-soluble. The water-soluble oligomers will be excreted directly or through various metabolic pathways. The water-insoluble oligomers will be taken up by macrophages and foreign body giant cells and further degraded in the lysosomes.

Because of the surfactant-like properties of these block copolymer systems, the diluted polymer solution forms a milky emulsion when the polymers loses its solubility in water. This self-emulsifying system is also of great interest because moderately hydrophobic drugs can be dissolved by the surface active triblock copolymers disclosed herein and then can be incorporated into emulsions (or suspensions) formed spontaneously at body temperature. The triblock copolymers can also be considered as degradable nonionic surfactants which are superior in function to the non-degradable Pluronic™ system. Certain peptides and proteins will also be adsorbed onto or entrapped into this system and formulated as a new type of controlled release delivery system. The drugs can be released slowly with degradation of the particles. Eventually, no further microencapsulating process, which are time-consuming and mostly requires organic solvents, is needed. The poly(ether-ester) block copolymers described in the present invention has temperature-sensitivity and has great potential for the development of the self-gelling or self-emulsifying, biodegradable depot system which can be injected extravascularly and release the incorporated or entrapped drug in a sustained manner.

As noted above, the biodegradable poly(ether-ester) block copolymers which the desirable thermally reversible gelation properties are those wherein the hydrophilic B block preferably makes up about 50 to 85% by weight of the copolymer and the hydrophobic A blocks makes up about 15 to 50% by weight of the copolymer. Also, the functional concentration at which these block copolymers are soluble at temperatures below their LCST may be considered may vary. When use for purposes of injection the block copolymer concentration may be as high as about 50% by weight with the only limitation be that of functionality. Taking into consideration the above discussions relative to the formation of emulsions and gels, concentrations in the range of about 3 to 40% are preferred and concentrations in the range of about 10–25% be weight are most preferred. The phase transition of the drug/copolymer combination above the LCST is the critical parameter required. Within the guidelines stated herein, one skilled in the art can determine, without undue experimentation, the appropriate drug loading, polymer composition and concentration, degradation rates, degree of gelation/emulsion formation, etc.

DETAILED DESCRIPTION OF PREFERRED EMBODIMENTS OF THE INVENTION

In order to illustrate preferred embodiments of this invention, schemes for synthesizing copolymers consisting of hydrophobic (A) and hydrophilic (B) blocks of the ABA type are illustrated. In both Schemes 1 and 2 the hydrophilic B block can be prepared using various molecular weights of poly(ethylene glycol) (PEG).

In Scheme 1, the preparation of a series of triblock copolymers is illustrated. Either a polylactide (PLA) or poly(ε-caprolactone)(PCL) can be prepared in a melt process by ring opening polymerization of lactide and ε-caprolactone initiated by reaction with PEG as follows:

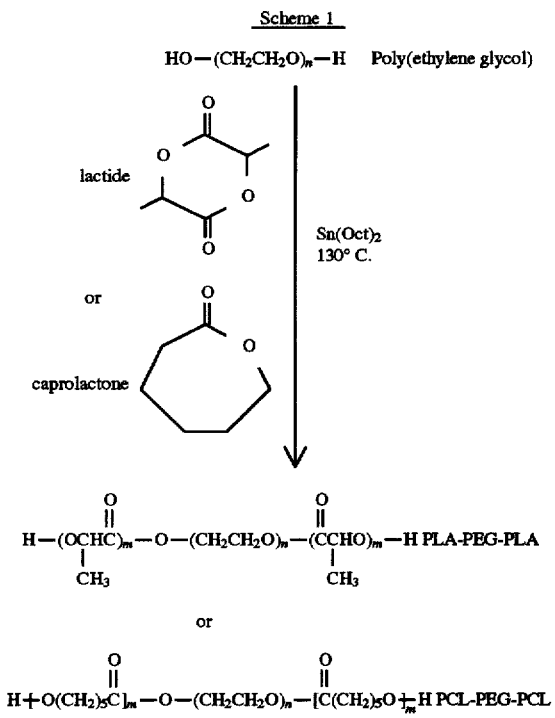

In a typical experiment, 3 g of lactide (or caprolactone) and stannous octoate (0.1 wt/wt % to monomer) is added into a reactor equipped with a high-vacuum valve containing an appropriate amount of PEG under dry nitrogen, and the reactor is tightly closed after evacuation. Polymerization is carried out at 130° C. for 30 hours. After cooling to room temperature, the reaction mixture is dissolved in methylene chloride followed by precipitation in an excess amount of diethyl ether. The product is dried under vacuum to a constant weight. The obtained copolymer are subjected to characterization using 1H-NMR (Bruker AS 200 FT spectrometer) and gel permeation chromatography using Ultrastyragel columns (Waters) calibrated with polystyrene standards. The overall molecular weights and compositions are determined by 1H-NMR. Properties of ABA block copolymers obtained by this process are shown in Table 2. The compositions for the copolymers were almost close to the values expected from the feed condition, indicating that polymerization was quantitative. The narrow, unimodal GPC traces demonstrated that no homopolymer was produced and that no side reaction such as chain scission and transesterification occurred.

TABLE 2

Results of bulk polymerization of lactide and caprolactone initiated by poly(ethylene glycol) at 130°C.

| Code | feed (PEG wt/wt %) | Copolymer Composition Calculated | Experimental* |
|---|---|---|---|
| PECL-1 | 50 | 500-1000-500 | 480-1000-480 |
| PELA-1 | 77 | 500-3400-500 | 510-3400-510 |
| PELA-2 | 63 | 1000-3400-1000 | 1080-3400-1080 |
| PELA-3 | 53 | 1500-3400-1500 | 1530-3400-1530 |

*calculated from 1H-NMR spectra
PECL: PCL-PEG-PCL triblock copolymer
PELA: PLA-PEG-PLA triblock copolymers All block copolymers shown in Table 2 were soluble in water at low temperature and showed solidification (thermosensitivity) as the temperature was elevated sufficiently. In all cases, the phase transition occurred instantly within a narrow temperature range. The transition temperatures of 5 wt/wt % aqueous solutions are presented in Table 3.

TABLE 3

Thermal transition temperatures of the various poly(ether-ester)block copolymer aqueous solutions (5 wt/wt %)

| Code | PEG content (wt/wt %) | Transition temperature (°C.) |
|---|---|---|
| PECL-1 | 50 | 10 |
| PELA-1 | 77 | 50 |
| PELA-2 | 63 | 40 |
| PELA-3 | 53 | 30 |

PECL: PCL-PEG-PCL triblock copolymer
PELA: PLA-PEG-PLA triblock copolymers

This kind of physical phenomenon is similar to the temperature-sensitivity found in surface-active block copolymers of poly(ethylene oxide)-poly(propylene oxide) (Pluronics™ or Poloxamer™) which are referenced above.

The system described herein shows both reverse thermal gelation and self-emulsification depending on polymer structure. A PCL-PEG multiblock copolymer formed according to Scheme 2, illustrated below, formed a semi-solid gel matrix on heating, while PCL-PEG-PCL triblock copolymer (PECL-1 shown in Table 2) formed an emulsion. These two different responses on thermal change are basically the same in regards to mechanism, and result from difference in concentration, temperature and polymer structure.

In Scheme 2, the preparation of a multiblock PEG-PCL copolymer is illustrated. A PEG polymer (MW≈1000) is reacted with an excess amount of hexamethylene diisocyanate (HMDI) in benzene at 60° C. to obtain an isocyanate (—N=C=O) group terminated PEG prepolymer. The PEG prepolymer is then further chain extended with a bifunctional polycaprolactone diol (MW≈530). The resulting product is a polyethylene glycol-polycaprolactone (PEG-PCL) multiblock copolymer with the blocks being connected by means of an urethane linkage. The reaction scheme is as follows:

Scheme 2

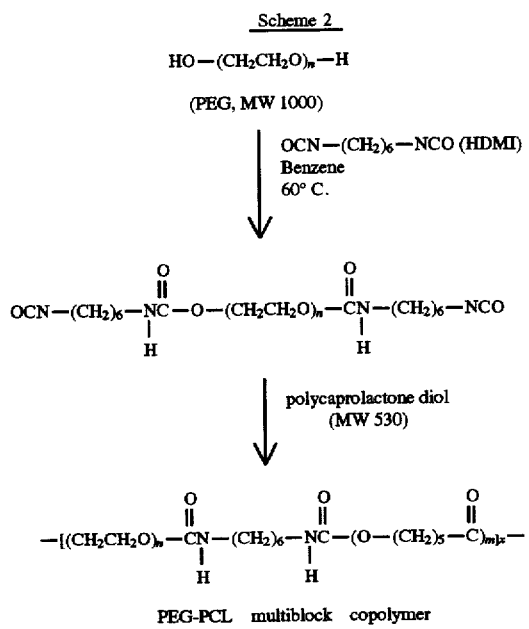

PEG-PCL multiblock copolymer

EXAMPLE 1

Synthesis of PECL-1

A mixture of 3 g of ε-caprolactone and stannous octoate (0.1 wt/wt % to monomer) was added into a reactor equipped with a high-vacuum valve containing an appropriate amount of PEG under dry nitrogen, and the reactor was tightly closed after evacuation. Polymerization was carried out at 130° C. for 30 hours. After cooling to room temperature, the reaction mixture was dissolved in methylene chloride followed by precipitation in an excess amount of diethyl ether. The product was dried under vacuum to a constant weight.

EXAMPLE 2

Synthesis of PELA-1,2,3.

A mixture of 3 g of lactide and stannous octoate (0.1 wt/wt % to monomer) was added into a reactor equipped with a high-vacuum valve containing an appropriate amount of PEG under dry nitrogen, and the reactor was tightly closed after evacuation. Polymerization was carried out at 130° C. for 30 hours. After cooling to room temperature, the reaction mixture was dissolved in methylene chloride followed by precipitation in an excess amount of diethyl ether. The product was dried under vacuum to a constant weight.

EXAMPLE 3

Poly(d,l-lactic acid) (MW≈2,500) (PLA) was synthesized by the conventional condensation polymerization of d, l-lactic acid at elevated temperature under reduced pressure. To the melt of this poly(d,l-lactic acid) was added polyethylene glycol (MW≈6,000) (PEG). The mixture was heated at 180° C. for 20 hours under a reduced pressure of about 50 mm Hg. with continuous bubbling of dry nitrogen gas to form a PLA-PEG-PLA block copolymer (average MW≈2500:6000:2500).

A one gram sample of the triblock copolymer was placed in a glass vial and 10 ml of ice-cold water was added. The polymer dissolved to yield a tan-colored liquid. The solution was heated to 37° C. in a water bath and was solidified to a non-flowing gel. After storing in a refrigerator for several hours, the gel again became a fluid, i.e. the polymer underwent reversible sol-gel transition. On heating the solution to 60° C., the polymer separated from the aqueous phase and formed as an opaque precipitate. On cooling in an ice water bath, the opaque precipitate became a transparent tan weight.

The above suggests that the PLA-PEG-PLA polymer is soluble in water at temperatures below the LCST, e.g., about 0° C., forms a gel when raised above the LCST, e.g., about 37° C., but collapses to form a precipitate when heated to about 60° C. The precipitate formed at 60° is sparingly soluble, or is at least slow to bring into solution, when cooled below the LCST. Such polymers, even though not completely soluble in cold solutions, may still be effective networks for injection or implantation into the body for the delivery of drugs as shown in Example 4.

EXAMPLE 4

To 0.2 g of the tan colored semi-solid gel obtained in Example 3 is mixed 0.1 ml of concentrated human calcitonin solution (10 mg/ml) by gentle blending with a spatula. The mixture is put into 10 mls of phosphate buffered saline (PBS) at 37° C. Fine polymeric calcitonin containing particles, having a diameter of between about 5 to 20 μm, are formed from the surface of the gel and slowly dispersed into the buffer to form a milky suspension of drug polymer microspheres.

The dilution of the polymeric gel and calcitonin blend in PBS formed a microsphere suspension that, when formulated under aseptic conditions, can be directly injected or implanted into the body.

When placed in the body, the calcitonin will be released slowly from the polymeric gel and diffuse out to the surrounding area and the polymer, being biodegradable, will be eliminated from the body.

EXAMPLE 5

Malic acid is polymerized with d,l-lactic acid to form a carboxyl group-containing oligomeric polyester (MW≈3,000). To a melt of this carboxylated copolymer is added polyethylene glycol (MW 5,000) which is predried under high vacuum at an elevated temperature and then further heated at 180° C. under a nitrogen atmosphere for 15 hours.

EXAMPLE 6

The block copolymer formed in Example 5 is dissolved in ice cold water and mixed with a solution of basic, heat stable platelet-derived growth factor (PDGF-B, isoelectric point 10.2). The mixture is injected to the mixing head of a T. K. Homomixer Mark II which is rotating at 10,000 rpm in a buffer solution at 500° C. The drug is incorporated into the copolymer by an simultaneous dispersion and precipitation process. The leaching of the drug during this process is reduced by the ionic interaction and complex formation between the carboxylated copolymer and the drug. The precipitated drug containing copolymer particles are collected and freeze dried.

EXAMPLE 7

An aliphatic poly(ethylene carbonate) polymer was synthesized by methods known in the art as follows. Carbon dioxide was reacted with ethylene oxide at 60° C. in a pressurized bomb reactor in the presence of diethyl zinc-water catalyst. The resulting polymer was purified by being dissolved in methylene chloride and reprecipitated in methanol. The purified high molecular weight poly(ethylene carbonate) (PEC) (average MW≈100,000) was refluxed in 1% HCl solution to obtain a low molecular weight poly (ethylene carbonate) (MW≈2,000) having hydroxyl groups at both ends of the polymer chain, e.g. a bifunctional diol.

Separately, polyethylene glycol (average MW≈3,400) was reacted with an excess amount of hexamethylene diisocyanate (HMDI) in benzene at 60° C. to obtain isocyanate (—N=C=O) group terminated prepolymer. The prepolymer was further chain extended with the bifunctional poly (ethylene carbonate) diol as prepared above. The resulting product was a polyethylene glycol-polyethylene carbonate (PEG-PEC) multiblock copolymer with the blocks being connected by means of an urethane linkage.

EXAMPLE 8

The multiblock copolymer synthesized in Example 7 is dissolved in ice cold water. Zinc insulin (PENTEX recombinant human insulin, zinc salt, is added to the PEG-PEC multiblock copolymer solution and gently mixed until a clear solution is obtained. The polymer/insulin salt solution is dropped into a buffered solution, pH of about 5.5 and at a temperature above the LCST (lower critical solution temperature) of the multiblock copolymer. Solidified multiblock copolymer/insulin beads are formed, collected by filtration and freeze dried.

Because of the hydrolyrically stable, but enzymatically degradable nature of the PEC block segment, the insulin release profile is different from the conventional hydrolyrically unstable block copolymers and the duration of insulin release is more extended.

EXAMPLE 9

Methoxy polyethylene glycol chloroformate (average MW≈2,000) is reacted with poly(ethylene carbonate) diol (MW≈2,000) obtained in Example 7 to form a BAB type block copolymer having PEG endblocks and possessing reversible thermal gelation properties. This block copolymer is enzymatically degradable due to the hydrophobic PEC central block segment.

The resulting polymer is dissolved in ice cold water and mixed with interleukin-2(IL-2) solution. Because of the marked hydrophobicity of the IL-2 protein, it can be stabilized by the hydrophobic interaction with the surfactant-like copolymer. The IL-2 polymer can be stored as an aqueous solution for extended periods of time due to the enzymatically degradable, but hydrolyrically stable nature of the copolymer. After gelling at body temperature, a much longer duration of drug release can be expected as compared to the non-degradable Pluronic™ or Poloxamer™ systems described in the prior art.

The above description will enable one skilled in the art to make and use drug loaded block copolymers based on reverse thermal gelation properties. The description is not intended to be an exhaustive statement of specific peptides, or other drugs which can be utilized and loaded onto the biodegradable block or multiblock copolymers. Neither are all block copolymers which may be prepared specifically shown. It will be apparent to one skilled in the art that various modifications may be made without departing from the scope of the inventions which is limited only by the following claims and their functional equivalents.

We claim:

1. An injectable biodegadable block copolymeric drug delivery liquid having reverse thermal gelation properties comprising an aqueous solution having uniformly contained therein between about 3 and 40% by weight of
   (a) an effective amount of a drug intimately contained in
   (b) a biodegradable block copolymer comprising
      (I) less than 50% by weight of a hydrophobic A polymer block comprising a member selected from the group consisting of poly(α-hydroxy acids) and poly(ethylene carbonates) and
      (ii) more than 50% by weight of a hydrophilic B polymer block comprising a polyethylene glycol; and
   wherein said liquid is maintained at a temperature below the lower critical solution temperature of said block copolymer.

2. An injectable drug delivery liquid according to claim 1 wherein said hydrophilic polyethylene glycol polymer block of said block copolymer has an average molecular weight of between 1000 and 20,000.

3. An injectable drug delivery liquid according to claim 2 wherein said hydrophilic polyethylene glycol polymer block comprises up to 85% by weight of said block copolymer and said hydrophobic A polymer block comprises at least 15% by weight of said block copolymer.

4. An injectable drug delivery liquid according to claim 3 wherein said hydrophobic A polymer block is a poly(α-hydroxy acid).

5. An injectable drug delivery liquid according to claim 4 wherein said poly(α-hydroxy acid) is a member derived or selected from the group consisting of poly(d,l-lactide), poly (l-lactide), poly(d,l-lactide-co-glycolide), poly(l-lactide-co-glycolide), poly(ε-caprolactone), poly(γ-butyrolactone), poly(δ-valerolactone), poly(ε-caprolactone-co-lactic acid), poly(ε-caprolactone-co-glycolic acid-co-lactic acid), hydroxybutyric acid, malic acid and bi- or terpolymers thereof.

6. An injectable drug delivery liquid according to claim 5 wherein said poly(α-hydroxy acid) polymer block has an average molecular weight of between about 500 and 10,000.

7. An injectable drug delivery liquid according to claim 6 wherein said hydrophobic poly(α-hydroxy acid) polymer A block has an average molecular weight of between about 500 and 3,000 and said hydrophilic polyethylene glycol polymer B block has an average molecular weight of between about 1,000 and 5,000.

8. An injectable drug delivery liquid according to claim 6 wherein said block copolymer is a triblock copolymer having a configuration selected from the group consisting of ABA and BAB block segments.

9. An injectable drug delivery liquid according to claim 8 wherein the hydrophobic A block segment contains a poly (α-hydroxy acid) selected from the group consisting of poly(d,l-lactide), poly(l-lactide), poly(d,l-lactide-co-glycolide), and poly (l-lactide-co-glycolide).

10. An injectable drug delivery liquid according to claim 8 wherein the hydrophobic A block segment contains a poly(α-hydroxy acid) consisting of poly(ε-caprolactone).

11. An injectable drug delivery liquid according to claim 3 wherein said hydrophobic polymer A block is a poly (ethylene carbonate) having an average molecular weight of between about 200 and 10,000.

12. An injectable drug delivery liquid according to claim 11 wherein said hydrophobic poly(ethylene carbonate) polymer A block has an average molecular weight of between about 200 and 3,000 and said hydrophilic polyethylene glycol polymer B block has an average molecular weight of between about 1,000 and 5,000.

13. An injectable drug delivery liquid according to claim 8 or 11 wherein said drug is a polypeptide.

14. An injectable drug delivery liquid according to claim 13 wherein said polypeptide is a member selected from the group consisting of oxytocin, vasopressin, adrenocorticotrophic hormone, epidermal growth factor, platelet-derived growth factor (PDGF), prolactin, luliberin or luteinising hormone releasing hormone, growth hormone, growth hormone releasing factor, insulin, somatostatin, glucagon, interleukin-2 (IL-2), interferon-α,β,γ (IFN-α,β,γ), gastrin, tetragastrin, pentagastrin, urogastroine, secretin, calcitonin, enkephalins, endorphins, angiotensins, thyrotropin releasing hormone (TRH), tumor necrosis factor (TNF), nerve growth factor (NGF), granulocyte-colony stimulating factor (G-CSF), granulocyte macrophage-colony stimulating factor (GM-CSF), macrophage-colony stimulating factor (M-CSF), renin, bradykinin, bacitracins, polymixins, colistins, tyrocidin, gramicidines, and synthetic analogues, modifications and pharmacologically active fragments thereof, monoclonal antibodies and soluble vaccines.

15. An injectable drug delivery liquid according to claim 8 or 11 wherein said drug is an anti-cancer agent.

16. An injectable drug delivery liquid according to claim 15 wherein said anti-cancer agent is a member selected from the group consisting of adriamycin, mitomycin, bleomycin, cisplatin, carboplatin, doxorubicin, daunorubicin, 5-fluorouracil, methotrexate, taxol, taxotere, and actinomycin D.

17. A method for the parenteral delivery of a drug in a biodegradable polymeric matrix to a warm blooded animal as a liquid with the resultant formation of a gel depot for the controlled release of said drug, which comprises;

(1) providing an injectable biodegradable block copolymeric drug delivery liquid having reverse thermal gelation properties comprising an aqueous solution having uniformly contained therein between about 3 and 40% by weight of (a) an effective amount of a drug intimately contained in (b) a biodegradable block copolymer having a LCST below the body temperature of said warm blooded animal and comprising (i) less than 50% by weight of a hydrophobic A polymer block comprising a member selected from the group consisting of poly(α-hydroxy acids) and poly(ethylene carbonates) and (ii) more than 50% by weight of a hydrophilic B polymer block comprising a polyethylene glycol;

(2) maintaining said liquid a temperature below the LCST of said block copolymer; and (3) injecting said liquid parenterally into said warm blooded animal forming a gel depot of said drug and biodegradable block polymer as the temperature of the liquid is raised by the body temperature of said animal to be above the LCST of said polymer.

18. A method according to claim 17 wherein said hydrophilic polyethylene glycol polymer block of said block copolymer has an average molecular weight of between 1000 and 20,000.

19. A method according to claim 18 wherein said hydrophilic polyethylene glycol polymer block comprises up to 85% by weight of said block copolymer and said hydrophobic A polymer block comprises at least 15% by weight of said block copolymer.

20. A method according to claim 19 wherein said hydrophobic A polymer block is a poly(α-hydroxy acid).

21. A method according to claim 20 wherein said poly (α-hydroxy acid) is a member derived or selected from the group consisting of poly(d,l-lactide), poly(l-lactide), poly(d, l-lactide-co-glycolide), poly(l-lactide-co-glycolide), poly(ε-caprolactone), poly(γ-butyrolactone), poly(δ-valerolactone), poly(ε-caprolactone-co-lactic acid), poly(ε-caprolactone-co-glycolic acid-co-lactic acid), hydroxybutyric acid, malic acid and bi- or terpolymers thereof.

22. A method according to claim 21 wherein said poly (α-hydroxy acid) polymer block has an average molecular weight of between about 500 and 10,000.

23. A method according to claim 22 wherein said hydrophobic poly(α-hydroxy acid) polymer A block has an average molecular weight of between about 500 and 3,000 and said hydrophilic polyethylene glycol polymer B block has an average molecular weight of between about 1,000 and 5,000.

24. A method according to claim 22 wherein said block copolymer is a triblock copolymer having a configuration selected from the group consisting of ABA and BAB block segments.

25. A method according to claim 24 wherein the hydrophobic A block segment contains a poly(α-hydroxy acid) selected from the group consisting of poly(d,l-lactide), poly (l-lactide), poly(d,l-lactide-co-glycolide), and poly(l-lactide-co-glycolide).

26. A method according to claim 24 wherein the hydrophobic A block segment contains a poly (α-hydroxy acid) consisting of poly (ε-caprolactone).

27. A method according to claim 19 wherein said hydrophobic polymer A block is a poly(ethylene carbonate) having an average molecular weight of between about 200 and 10,000.

28. A method according to claim 27 wherein said hydrophobic poly(ethylene carbonate) polymer A block has an average molecular weight of between about 200 and 3,000 and said hydrophilic polyethylene glycol polymer B block has an average molecular weight of between about 1,000 and 5,000.

29. A method according to claim 24 or 25 wherein said drug is a polypeptide.

30. A method according to claim 29 wherein said polypeptide is a member selected from the group consisting of oxytocin, vasopressin, adrenocorticotrophic hormone, epidermal growth factor, platelet-derived growth factor (PDGF), prolactin, luliberin or luteinising hormone releasing hormone, growth hormone, growth hormone releasing factor, insulin, somatostatin, glucagon, interleukin-2 (IL-2), interferon-α,β,γ (IFN-α,β,γ), gastrin, tetragastrin, pentagastrin, urogastroine, secretin, calcitonin, enkephalins, endorphins, angiotensins, thyrotropin releasing hormone (TRH), tumor necrosis factor (TNF), nerve growth factor (NGF), granulocyte-colony stimulating factor (G-CSF), granulocyte macrophage-colony stimulating factor (GM-CSF), macrophage-colony stimulating factor (M-CSF), renin, bradykinin, bacitracins, polymixins, colistins, tyrocidin, gramicidines, and synthetic analogues, modifications and pharmacologically active fragments thereof, monoclonal antibodies and soluble vaccines.

31. A method according to claim 24 or 25 wherein said drug is an anti-cancer agent.

32. A method according to claim 31 wherein said anti-cancer agent is a member selected from the group consisting of adriamycin, mitomycin, bleomycin, cisplatin, carboplatin, doxorubicin, daunorubicin, 5-fluorouracil, methotrexate, taxol, taxotere, and actinomycin D.

* * * * *